(12) United States Patent
Polukhtin

(10) Patent No.: US 10,407,436 B2
(45) Date of Patent: Sep. 10, 2019

(54) CARBOXAMIDE-SUBSTITUTED XANTHENE DYES

(71) Applicant: Andrei Polukhtin, Scottsdale, AZ (US)

(72) Inventor: Andrei Polukhtin, Scottsdale, AZ (US)

(*) Notice: Subject to any disclaimer, the term of this patent is extended or adjusted under 35 U.S.C. 154(b) by 159 days.

(21) Appl. No.: 14/734,984

(22) Filed: Jun. 9, 2015

(65) Prior Publication Data

US 2016/0362418 A1 Dec. 15, 2016

(51) Int. Cl.
C07D 491/147 (2006.01)
C09K 11/06 (2006.01)

(52) U.S. Cl.
CPC .......... *C07D 491/147* (2013.01); *C09K 11/06* (2013.01); *C09K 2211/1048* (2013.01); *C09K 2211/1088* (2013.01)

(58) Field of Classification Search
CPC .................................. C07D 491/147
See application file for complete search history.

(56) References Cited

FOREIGN PATENT DOCUMENTS

| WO | WO-9803497 A1 | * | 1/1998 | ............. C07C 69/00 |
| WO | WO-2009046165 A1 | * | 4/2009 | ............ C07D 413/08 |

* cited by examiner

Primary Examiner — Andrew D Kosar
Assistant Examiner — John S Kenyon
(74) Attorney, Agent, or Firm — Birch, Stewart, Kolasch & Birch, LLP

(57) ABSTRACT

Carboxamide-substituted xanthene dyes, reactive dyes, and the use of such dyes as a labeling reagent are disclosed. Specifically, a carboxamide-substituted dye of the formula (I)

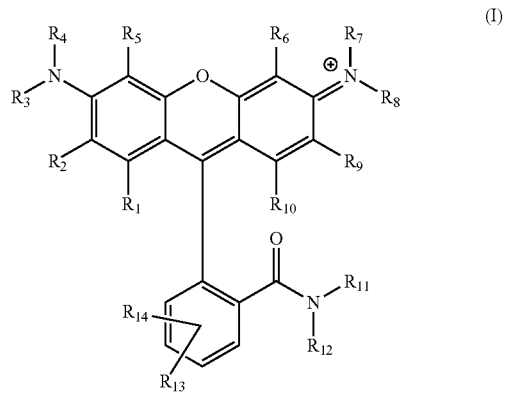

is disclosed.

6 Claims, 1 Drawing Sheet

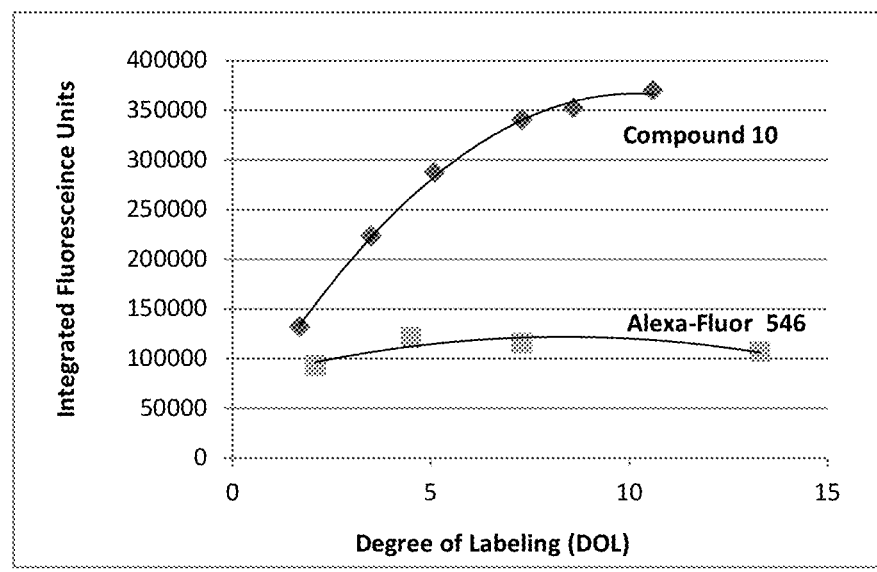

CARBOXAMIDE-SUBSTITUTED XANTHENE DYES

BACKGROUND OF THE INVENTION

1. Field of the Invention

The present invention discloses xanthene-based, carboxamide-substituted dyes of the general formula (I) as well as the preparation, activation, and use of said dyes.

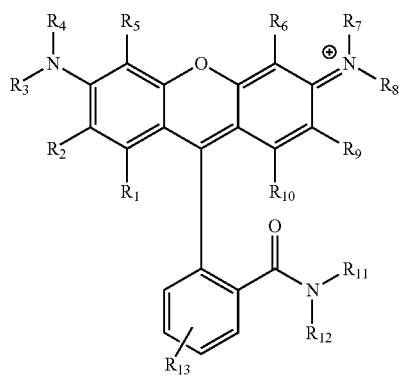

(I)

2. Description of the Background

Organic fluorescent compounds, also known as dyes, are widely used as sensitive detection reagents in biological systems. Xanthene-type dyes are among the most frequently organic fluorescent compounds used as detection reagents due to their very good spectral properties and photostability. The dyes having a very high fluorescence quantum yield are especially important since the fluorescence enables the labeled analyte to be detected at very high sensitivity.

Many xanthene-type dyes possess a carbonyl group at the o-position of the "lower" aromatic ring, which causes the formation of a colorless lactone under some physiological conditions. The lactone is colorless and non-fluorescent. Thus, the labeled analyte cannot be detected by means of fluorescent spectroscopy.

Scheme 1

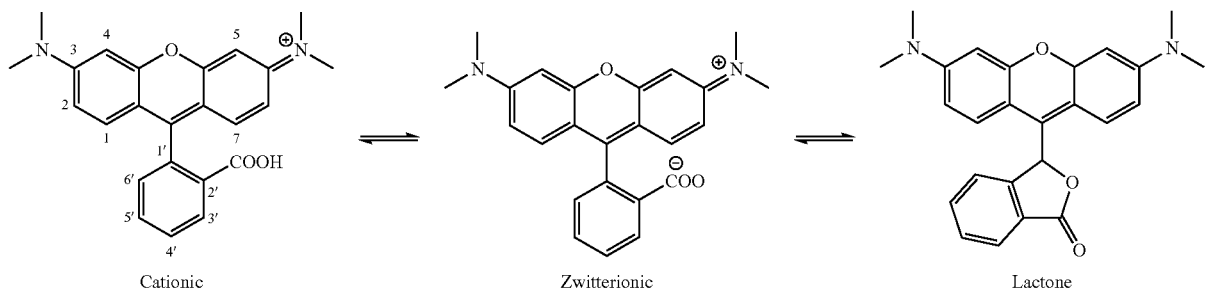

Cationic          Zwitterionic          Lactone

The dyes according to formula (I) have very good spectral properties, such as the position of the absorbance and emission bands, high extinction coefficient, high fluorescent quantum yields, and photostability. The disadvantage of lactone or lactam formation, which is associated with the presence of carboxylic acid at the $2^{nd}$ position of the "lower" aromatic ring, is prevented by the conversion of said carboxylic acid group into a secondary amide.

The dyes of this invention possess considerable advantage over their previously described xanthene dyes. In particular, their fluorescence yields are typically higher than those of other dyes having compatible spectra, including fluorescein, Cy-2, tetramethylrhodamine, Cy-3, and Texas Red. In addition, the dyes of this invention exhibit enhanced resistance to quenching upon protein conjugation, and protein conjugates with the dyes of the invention typically possess substantially higher fluorescence yields than that achieved with most commercially available fluorescent dyes, including AlexaFluor dyes. Also, the dyes of this invention are substantially more water-soluble than dyes without an amido-sulfoalkyl group.

The traditional way to covalently attach a fluorescent dye to a biomolecule is through a reaction of a primary amine group of the biomolecule with an activated ester, for example dyes of NHS ester. One way of rendering the formation of non-fluorescent lactone is to use the carboxylic group o-position of the "lower" aromatic ring for covalent attachment of a fluorescent dye to the biomolecule. However, this reaction produces a primary amide, which immediately rearranges into a lactam according to Scheme 1.

The lactam is colorless and non-fluorescent under physiologically relevant conditions. Thus, the labeled analyte cannot be detected by means of fluorescent spectroscopy.

WO 02/055512 and US 2006/0154251 A disclose the preparation of amide derivatives of fluorescein and rhodamine dyes, which comprise the conversion of carboxylic acids into activated esters followed by reaction of said activated esters with a secondary amine under reflux conditions to form secondary amides. Even though the disclosed secondary amides do not form non-fluorescent lactone or rearrange into lactam, they possess several major shortcomings. First, the disclosed secondary amides are known to undergo hydrolysis under basic conditions (Boyarskiy, V. P. et al., Chem. Eur. J., 14:1784, 2008), resulting in dissociation of a fluorescent dye from an analyte, so the dissociated fluorescent dye will be detected by means of fluorescent spectroscopy and not the labeled biomolecule of interest. Second, conversion of a carboxylic acid into a secondary amide makes the dye molecule less hydrophilic, which in turn increases the aggregation of labeled biomolecules in aqueous media and increases the tendency for forming non-fluorescent dye-dye dimers.

Therefore, there is a need for xanthene class fluorescent dyes that do not undergo formation of non-fluorescent lactone/lactam and, at the same time, do not undergo hydrolysis in aqueous media.

SUMMARY OF THE INVENTION

In a first embodiment, the present invention is directed to a carboxamide-substituted, lipophilic dye of the formula (I)

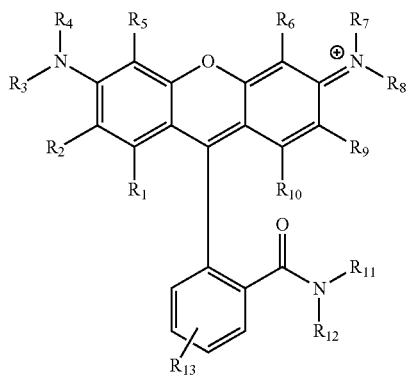

(I)

$R_1$, $R_2$, $R_5$, $R_6$, $R_9$ and $R_{10}$ are independently H or halogen, $R_3$, $R_4$, $R_7$, and $R_8$ are independently H or $C_1$-$C_5$. Alternatively, $R_3$ in combination with $R_2$ and/or $R_8$ in combination with $R_9$ form a 5- or 6-membered saturated or unsaturated ring that is optionally substituted with a $C_1$-$C_5$. Optionally, $R_4$ in combination with $R_5$ and/or $R_6$ in combination with $R_7$ form a 5- or 6-membered saturated ring that is optionally substituted with a $C_1$-$C_5$ alkyl.

$R_{11}$ and $R_{12}$ are independently $C_1$-$C_{18}$ alkyl, branched or cyclic saturated or unsaturated hydrocarbon group having up to 300 carbon atoms that is optionally interrupted by O or N atoms, optionally further substituted with F, Cl, Br, I, a carboxylic acid, a salt of carboxylic acid, or a carboxylic acid ester, $R_{13}$ is a reactive group that is capable of modifying biomolecules, and $R_{14}$ is hydrogen or halogen.

In a second embodiment, the present invention is directed to a hydrophilic, carboxamide-substituted dye of the formula (I) in which:

$R_1$ through $R_{10}$, $R_{13}$, and $R_{14}$ are as described above, $R_{11}$ and $R_{12}$ are independently polyethylene glycol having a formula weight of 100-20000 Da or $C_1$-$C_{18}$ alkyl.

In a third embodiment, the present invention is directed to a hydrophilic, carboxamide-substituted dye of the formula (I) that contains at least one charged group in which:

$R_1$, $R_2$, $R_5$, $R_6$, $R_9$ and $R_{10}$ are independently H; halogen; $SO_3X$; or $SO_2NH$—$(CH_2)_n$—$SO_3X$, where n=2-5, and X is H or a counterion, $R_3$, $R_4$, $R_7$, and $R_8$ are independently H or $C_1$-$C_5$ alkyl where each alkyl is optionally further substituted with $SO_3X$. Alternatively, $R_3$ in combination with $R_2$ and/or $R_8$ in combination with $R_9$ form a 5- or 6-membered saturated or unsaturated ring that is optionally substituted with a $C_1$-$C_5$ alkyl where each alkyl is optionally further substituted with $SO_3X$. Optionally, $R_4$ in combination with $R_5$ and/or $R_6$ in combination with $R_7$ form a 5- or 6-membered saturated ring that is optionally substituted with a $C_1$-$C_5$ alkyl.

$R_{11}$ and $R_{12}$ are independently $(CH_2)_n SO_3X$, where X is H or a counterion, and n=2-4, or a $C_1$-$C_{18}$ alkyl optionally further substituted with a carboxylic acid, a salt of carboxylic acid, $SO_3X$, or $PO_3X$, $R_{13}$ is a reactive group, and $R_{14}$ is hydrogen or halogen.

More specifically, $R_{11}$ and $R_{12}$ may be independently $C_1$-$C_{18}$ alkyl and $(CH_2)_n$—$SO_3X$ where X is H or a counterion and n is 2, 3, or 4. $R_{11}$ and $R_{12}$ may be independently discrete or non-discrete polyethylene glycol.

In a fourth embodiment, the present invention is directed to heterobifunctional dyes of the general formula (I) where:

$R_1$ through $R_{10}$, $R_{13}$, and $R_{14}$ are as described above, $R_{11}$ and $R_{12}$ may be independently a group consisting of orthogonal reactive pairs which undergo Staudinger ligation, copper-catalyzed Huisgen 1,3-dipolar cycloaddition, strain-promoted Huisgen 1,3dipolar cycloaddition, Inverse Electron Demand Diels-Alder cycloaddition, and hydrazone or oxime bond forming reactions.

In a fifth embodiment, the present invention is directed to a carboxamide-substituted dye of the formula:

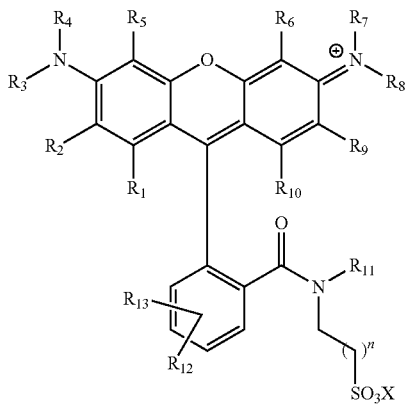

in which:

$R_1$, $R_2$, $R_9$ and $R_{10}$ are independently hydrogen or halogen, $R_5$ and $R_6$ are independently hydrogen, $SO_3X$, or $SO_2NH$—$(CH_2)_n$—$SO_3X$, where X is H or a counterion, and n=2-5, $R_3$, $R_4$, $R_7$, and $R_8$ are independently H or $C_1$-$C_5$ alkyl, where each alkyl is optionally further substituted with halogen or $SO_3X$, where X is H or a counterion, $R_{11}$ is $C_1$-$C_{18}$ alkyl, branched or cyclic saturated or unsaturated hydrocarbon group having up to 300 carbon atoms that is optionally interrupted by O or N atoms, optionally further substituted with F, Cl, Br, I, a carboxylic acid, a salt of carboxylic acid, or a carboxylic acid ester, $SO_3X$, or $PO_3X$, where X is H or a counterion, $R_{12}$ is a reactive group, and $R_{13}$ is hydrogen or halogen.

More specifically, $R_{11}$ may be discrete or non-discrete polyethylene glycol. $R_{12}$ may be a biomolecule.

In a sixth embodiment, the present invention is directed to a carboxamide-substituted dye of the formula:

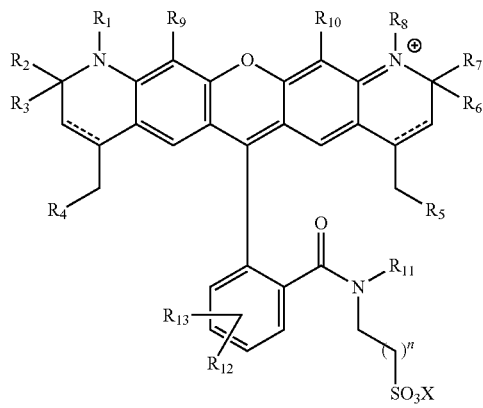

in which:

$R_1$, $R_2$, $R_3$, $R_6$, $R_7$, and $R_8$ are independently hydrogen, or $C_1$-$C_5$ alkyl, where each alkyl is optionally further substituted with halogen or $SO_3X$, where X is H or a counterion, $R_9$ and $R_{10}$ are independently hydrogen, $SO_3X$, or $SO_2NH$—$(CH_2)_n$—$SO_3X$, where X is H or a counterion, and n=2-5, $R_4$ and $R_5$ are independently hydrogen, —$CH_3$, or $SO_3X$, where X is H or counterion, $R_{11}$ is $C_1$-$C_{18}$ alkyl, branched or cyclic saturated or unsaturated hydrocarbon group having up to 300 carbon atoms that is optionally interrupted by O or N atoms, optionally further substituted with F, Cl, Br, I, a carboxylic acid, a salt of carboxylic acid, or a carboxylic acid ester, $SO_3X$, or $PO_3X$, where X is H or a counterion, $R_{12}$ is a reactive group, and $R_{13}$ is hydrogen or halogen.

More specifically, $R_{11}$ may be discrete or non-discrete polyethylene glycol. $R_{12}$ may be a biomolecule.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to one of ordinary skill in the art from this detailed description.

BRIEF DESCRIPTION OF THE FIGURES

The present invention will become more fully understood from the detailed description given below and the accompanying drawing that is given by way of illustration only and is thus not limitative of the present invention.

FIG. 1 is a fluorescence emission spectra of IgG conjugates of Compound 5 and Alexa Dye 546 at similar degrees of substitution and equal optical densities.

DETAILED DESCRIPTION OF THE INVENTION

The present invention will now be described with reference to the accompanying drawing.

Unless defined otherwise, all terms used herein have the same meaning as is commonly understood by one of ordinary skill in the art to which this invention belongs. All patents, patent applications, and publications referred to throughout the disclosure herein are incorporated by reference in their entirety. In the event that there is a plurality of definitions for a term herein, those definitions in this section prevail.

The term "biomolecule" as used herein refers to a compound of biological origin or of biological activity. Biomolecules include, for example, a nucleic acid, a nucleotide, a protein, an amino acid, a carbohydrate monomer, and a polysaccharide. If the biomolecule is a nucleic acid, it may be DNA, cDNA, RNA, or PNA and may comprise natural or unnatural bases or internucleotide linkages, such as phosphodiesters, phosphorothioates, phosphoramidites, or peptide nucleic acids.

The term "reactive moiety" or "reactive group" herein refers to a moiety that can be coupled with another moiety without prior activation or transformation. Some commercially sold molecules referred to herein as linking moieties include those that react with free amines on the target molecule, such as N-hydroxysuccinimidyl, p-nitrophenyl, pentafluorophenyl and N-hydroxybenzotriazolyl ester, and those that react with free sulfhydryls present on the target molecule such as maleimido, alpha-haloacetamido and pyridyldisulfides.

The term "linker" is a covalent linkage having 1-48 nonhydrogen atoms selected from the group consisting of C, N, O, P, and S and composed of any combination of single, double, triple or aromatic carbon-carbon bonds, carbon-nitrogen bonds, nitrogen-nitrogen bonds, carbon-oxygen bonds, carbon-sulfur bonds, phosphorus-oxygen bonds, and phosphorus-nitrogen bonds. The non-cleavable linker is preferably (i) a divalent linear —$(CH_2)_x$— group or a —$(CH_2CH_2O)_x$— group wherein x is 1 to 25, (ii) a branched or cyclic alkane group, which is optionally substituted by at least one atom selected from the group consisting of oxygen, substituted nitrogen, and sulfur, or (iii) absent. The non-cleavable linker is more preferably an alkyl having 1-6 carbon atoms or a discrete or non-discrete polyethylene glycol linker.

The term "ligand/receptor couple" as used herein refers to a pair of molecules having a substantially high affinity for binding specifically to one another. One example of such a binding pair would be a cell receptor and the ligand that binds that receptor. Another example would be biotin and avidin, which are two molecules that have a strong affinity for binding each other and having an association constant of around $10^{15}$. Other pairs include Peptide S and ribonuclease A, digoxigenin and its receptor and complementary oligonucleotide pairs.

Various methods exist which may be employed to bind the extended linking group to a macromolecule or fragment. For example, to facilitate this binding, the extended linking group may be attached to biomolecule-reactive groups, such as active ester groups, amino groups, sulfhydryl groups, carbohydrate groups, azido groups or carboxy groups. A variety of methodologies exist for reacting biomolecule-reactive groups with macromolecules or macromolecule fragments. Examples of such methodologies are photo-crosslinking and glutaraldehyde crosslinking Still other methods for affecting such coupling will occur to those skilled in the art. See, for examples of such methods: Hermanson, G. T., Bioconjugate Techniques, Elsevier Science, London, 2008.

Active ester groups of the present invention may be selected such that they will not impair linkage of the extended linking group to a protein or macromolecule. Those skilled in the art will appreciate that active esters such as, for example, N-hydroxysuccinimide or N-hydroxysulfo-succinimide may be employed in the present invention. Alternatively, primary amino groups on the extended linking group may be coupled to primary amino groups on a protein by glutaraldehyde. Amino groups on proteins may be coupled to carboxy groups on the extended linking group. In addition, the extended linking group may be modified with a nitrophenylazide such that coupling to a protein will occur when irradiated with visible light. Still other methods for affecting such coupling will occur to those skilled in the art.

The present invention describes xanthene-based, carboxamide-substituted dyes of the general formula (I) as well as the preparation, activation, and use of said dyes. The dyes of this invention possess a reactive group $R_{13}$ useful for preparation of fluorescent conjugates.

The compounds of this invention are rhodamines in which a carboxyl group at the 2' position is converted into secondary amide in order to prevent formation of non-fluorescent lactone. The second carboxylic group at the 5' or 6' position is optionally converted into a reactive group useful for preparing fluorescent conjugates.

One preferred embodiment of the present invention relates to lipophilic dyes of the general formula (I):

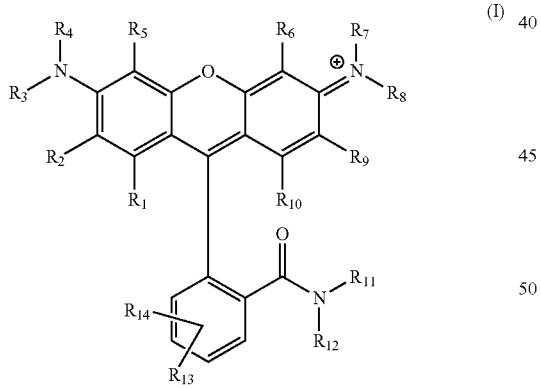

in which:
$R_1$, $R_2$, $R_5$, $R_6$, $R_9$ and $R_{10}$ are independently hydrogen or halogen,
$R_3$, $R_4$, $R_7$, and $R_9$ are independently H or $C_1$-$C_5$ alkyl where each alkyl is optionally further substituted with halogen,
$R_{11}$ and $R_{12}$ are independently a straight-chain, branched or cyclic saturated or unsaturated hydrocarbon group having up to 30 carbon atoms that is optionally interrupted by O or N atoms,
$R_{13}$ is a reactive group or a biomolecule, and
$R_{14}$ is hydrogen or halogen.

Exemplary reactive groups of $R_{13}$ are given in Table 1.

TABLE 1

| Reactive Group | Target Functional Group |
| --- | --- |
| Carbodiimide | Amine/Carboxyl |
| Carbonyl | Hydrazine |
| Diazirine | Nonselective |
| Hydrazide | Carbohydrate (oxidized) |
| Hydroxymethyl Phosphine | Amine |
| Imidoester | Amine |
| NHS-ester | Amine |
| PFP-ester | Amine |
| Psoralen | Amine |
| Pyridyl Disulfide | Sulfhydryl |
| Vinyl Sulfone | Sulfhydryl, amine, hydroxyl |
| Terminal Alkyne | Azide |
| Azide | Terminal alkyne, cyclooctyne |
| Trans-Cyclooctene | Tetrazine |

To one skilled in the art, it will be apparent that there are multiple variations of reactive groups useful for modifying a biomolecule with fluorescent dyes.

In yet another preferred embodiment of the present invention the lipophilic dyes has the general formula (II):

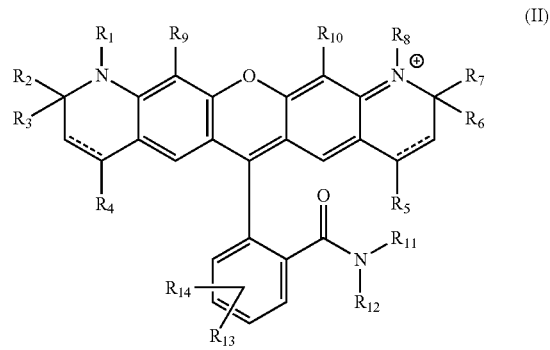

in which:
$R_1$, $R_2$, $R_3$, $R_6$, $R_7$, $R_8$, $R_9$, and $R_{10}$ are independently hydrogen or $C_1$-$C_5$ alkyl,
$R_4$ and $R_5$ are independently hydrogen or $CH_3$,
$R_{11}$ and $R_{12}$ are independently a straight-chain, branched or cyclic saturated or unsaturated hydrocarbon group having up to 30 carbon atoms that is optionally interrupted by O or N atoms,
$R_{13}$ is a reactive group, and
$R_{14}$ is hydrogen or halogen.

The lipophilic dyes of the general formula (I) and (II) are soluble in non-polar media and biological membranes and may be employed, for example, for detecting membrane properties or for measuring molecular distances.

In yet another embodiment, the present invention relates to hydrophilic dyes of the general formula (I) that contain a polyethylene glycol:

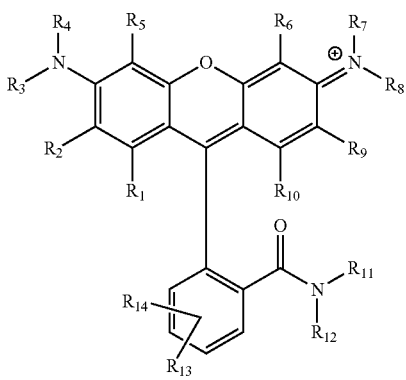

(I)

in which:
- $R_1$, $R_2$, $R_5$, $R_6$, $R_9$ and $R_{10}$ are independently hydrogen, halogen, or $SO_2NH$—$R_{15}$, where $R_{15}$ is polyethylene glycol having a formula weight of 100-20000 Da,
- $R_3$, $R_4$, $R_7$, and $R_9$ are independently H or $C_1$-$C_5$ alkyl,
- $R_{11}$ and $R_{12}$ are independently polyethylene glycol having a formula weight of 100-20000 Da or $C_1$-$C_{18}$ alkyl,
- $R_{13}$ is a reactive group or a biomolecule, and
- $R_{14}$ is hydrogen or halogen.

In yet another preferred embodiment of the present invention, the hydrophilic dyes has the general formula (II):

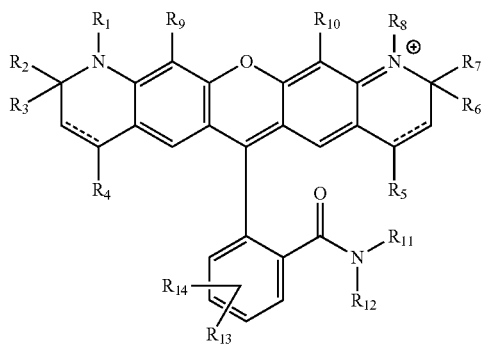

(II)

in which:
- $R_1$, $R_2$, $R_3$, $R_6$, $R_7$ and $R_8$ are independently hydrogen or $C_1$-$C_3$ alkyl,
- $R_4$ and $R_5$ are independently hydrogen, $CH_3$, or $CH_2$—$SO_2NH$—$R_{15}$, where $R_{15}$ is polyethylene glycol having a formula weight of 100-20000 Da,
- $R_9$ and $R_{10}$ are independently hydrogen or $SO_2NH$—$R_{15}$, where $R_{15}$ is polyethylene glycol having a formula weight of 100-20000 Da,
- $R_{11}$ and $R_{12}$ are independently polyethylene glycol having a formula weight of 100-20000 Da or $C_1$-$C_{18}$ alkyl,
- $R_{13}$ is a reactive group or a biomolecule, and
- $R_{14}$ is hydrogen or halogen.

The hydrophilic dyes of the general formula (I) or (II) have good solubility in aqueous media and contain no negative charges. The use of such hydrophilic dyes achieves a high degree of labeling of biomolecules, for example proteins, without aggregating/precipitating the biomolecules and without substantially changing the isoelectric point of the biomolecules. For example, IgG was labeled with Compound 4 of the invention (see Table 2 below) with a very high degree of substitution without precipitating the IgG. On the other hand, an attempt to achieve a similar degree of substitution using a structurally similar compound of US 2006/0154251A (Atto-Tec Dye 556) resulted in complete precipitation of the IgG.

Surprisingly, it was possible to provide dyes, which functionalized differently with various combinations of $R_{11}$ and $R_{12}$ according to the general formula (I) and which have very good spectral properties, such as the position of absorbance and fluorescence peaks, high extinction coefficient and high quantum yields. The disadvantage of lactone or lactam formation, which occurs with conventional dyes having a carboxylic acid at the 2' position, is prevented by converting said carboxylic acid group into a secondary amide.

The spectral properties of dyes can be tuned by modifying the rhodamine core of dyes. Several properties of such dyes are given in Table 2.

TABLE 2

| Fluorescent dyes | Abs/Em |
|---|---|
| Compound 1 | 518/539 |
| Compound 2 | 531/551 |
| Compound 3 | 556/573 |

TABLE 2-continued

| Fluorescent dyes | Abs/Em |
|---|---|
| 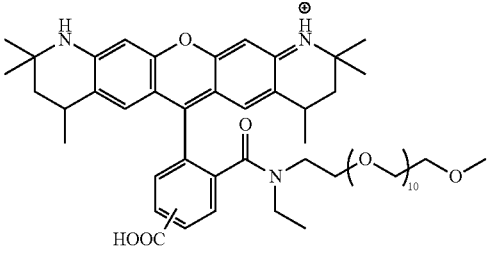 Compound 4 | 556/573 |
| 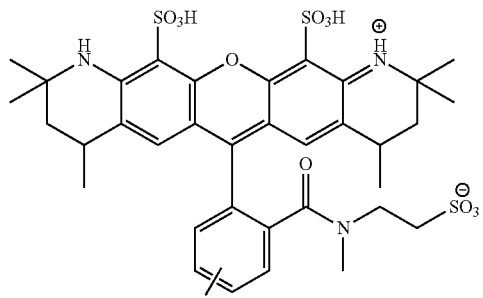 Compound 5 | 546/562 |
| 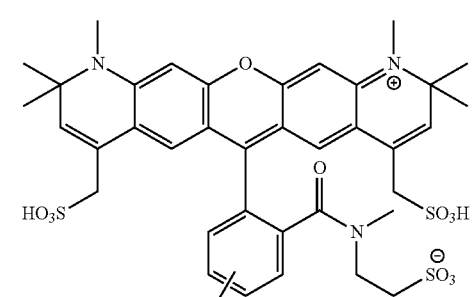 Compound 6 | 601/623 |

Importantly, the introduction of the carboxamide group does not substantially alter spectral property of dyes, such as the position of the absorbance and fluorescence peaks, the high extinction coefficient and the high quantum yields. It was merely observed that the absorption and emission maxima of some dyes red-shifted by 10 nm on average.

The dyes of this invention possess considerable advantages over carboxamide dyes disclosed in WO 02/055512 and US 2006/0154251 A, where the carboxamide group at the 2' position is used to connect the dyes with biomolecules of interest. The carboxamide group at the 2' position is susceptible to hydrolysis under basic conditions (Boyarskiy, V. P. et al., Chem. Eur. J., 14:1784 2008). However, hydrolysis of carboxamide dyes, in which the carboxamide group at the 2' position is used to connect the dyes with biomolecules of interest, results in dissociation of the fluorescent dye from an analyte. As such, the dissociated fluorescent dye will be detected by means of fluorescent spectroscopy rather than the labeled biomolecule of interest. The hydrolysis of carboxamide dyes of this invention will not result in dissociation of the dyes from the biomolecule of interest. Rather, the hydrolysis of carboxamide dyes of this invention will only result in a slight change in spectral properties of the conjugated dyes.

The properties of the dyes can be fine tuned by introducing various moieties at the amide group. Thus, it is possible, for example, to increase the lipophilicity of the dyes by introducing a long alkyl chain as a moiety at the amide group. On the other hand, it is possible to increase the hydrophilicity of the dyes by introducing a sugar residue or a long polyethylene glycol chain. Importantly, the dyes of this invention allow for the incorporation of a long polyethylene glycol chain without distancing the fluorescent dye from the conjugated biomolecule. Incorporation of a long polyethylene glycol chain into carboxamide dyes is disclosed in WO 02/055512 and US 2006/0154251 A; however, the method used in these references possesses two major shortcomings. First, it will result in substantial distancing of the fluorescent dye from the conjugated biomolecule, for example, when mPEG 5000 or mPEG 10000 is used. Such distancing is very undesirable in some applications. Second, it is synthetically challenging and impractical to make such compounds.

In yet another embodiment, the present invention relates to hydrophilic dyes of the general formula (I) that possess at least one negative charge.

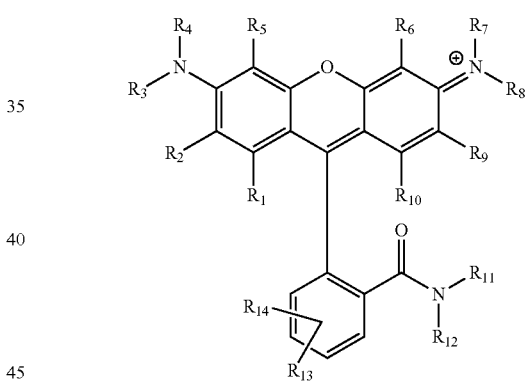

in which:

$R_1$, $R_2$, $R_5$, $R_6$, $R_9$ and $R_{10}$ are independently hydrogen, halogen, $SO_3X$, or $SO_2NH$—$(CH_2)_n$—$SO_3X$, where n=2-5, and X is H or a counterion. Examples of suitable counterions include $K^+$, $Na^+$, $Cs^+$, $Li^+$, $Ca^{2+}$, $Mg^{2+}$, ammonium, alkylammonium, alkoxyammonium salts, or pyridinium salts.

$R_3$, $R_4$, $R_7$, and $R_8$ are independently H or $C_1$-$C_5$ alkyl, where each alkyl is optionally further substituted with $SO_3X$.

$R_{11}$ and $R_{12}$ are independently $(CH_2)_nSO_3X$, where X is H or a counterion, and n=2-4, or a $C_1$-$C_{18}$ alkyl optionally further substituted with a carboxylic acid, a salt of carboxylic acid, $SO_3X$, or $PO_3X$, $R_{13}$ is a reactive group or a biomolecule, and $R_{14}$ is hydrogen or halogen.

In yet another preferred embodiment of the present invention, the hydrophilic dyes has the general formula:

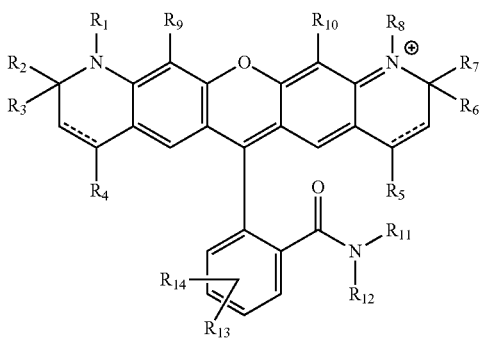

in which:

$R_1$, $R_2$, $R_3$, $R_6$, $R_7$ and $R_8$ are independently hydrogen, $C_1$-$C_5$ alkyl optionally further substituted with $SO_3X$, where n=2-5, and X is H or a counterion. Examples of suitable counterions include $K^+$, $Na^+$, $Cs^+$, $Ca^{2+}$, $Mg^{2+}$, ammonium, alkylammonium, alkoxyammonium salts, or pyridinium salts.

$R_4$ and $R_5$ are independently hydrogen, $CH_3$, or $CH_2SO_3X$, where X is H or counterion, $R_9$ and $R_{10}$ are independently hydrogen or $SO_3X$, where X is H or counterion, $R_{11}$ and $R_{12}$ are independently $(CH_2)_nSO_3X$, and n=2-4, or a $C_1$-$C_{18}$ alkyl optionally further substituted with a halogen, carboxylic acid, a salt of carboxylic acid, $SO_3X$, or $PO_3X$, where X is H or counterion, $R_{13}$ is a reactive group or a biomolecule, and $R_{14}$ is hydrogen or halogen.

The fluorescence yield of protein-dye conjugates of the hydrophilic dyes of this invention are usually substantially higher than those of structurally and spectrally similar dyes having a carboxyl group at the 2' position of the "lower" aromatic ring. The enhanced fluorescence is presumably a result of its inability to undergo formation into non-fluorescent lactones and lactams. The comparison of fluorescence yields of IgG labeled with Compound 5 and with structurally and spectrally similar Alexa Fluor 546 dye at a similar degree of substitution and equal optical density revealed that Compound 5 has substantially increased resistance to quenching upon protein conjugation as shown in FIG. 1.

In still another aspect, the present invention relates to heterobifunctional dyes of the general formula (I)

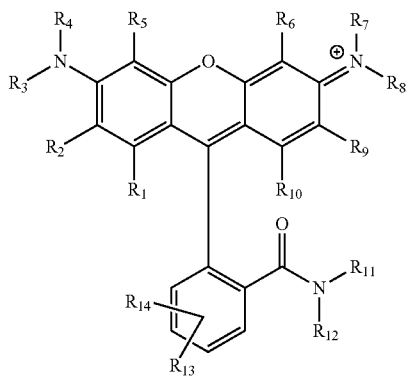

in which:

$R_1$, $R_2$, $R_5$, $R_6$, $R_9$ and $R_{10}$ are independently hydrogen, halogen, $SO_3X$, or $SO_2NH$—$(CH_2)_nSO_3X$, where n=2-5, and X is H or a counterion. Examples of suitable counterions include $K^+$, $Na^+$, $Cs^+$, $Li^+$, $Ca^{2+}$, $Mg^{2+}$, ammonium, alkylammonium, alkoxyammonium salts, or pyridinium salts.

$R_3$, $R_4$, $R_7$, and $R_8$ are independently H or $C_1$-$C_5$ alkyl, where each alkyl is optionally further substituted with $SO_3X$.

$R_{11}$ and $R_{12}$ are independently a reactive moiety partner of a pair of orthogonally reactive moieties that can react with each other in the presence or absence of a catalyst without activation and both reactive moieties are sufficiently stable under commonly applied biomolecule labeling conditions or $C_1$-$C_{18}$ alkyl optionally further substituted with a carboxylic acid, a salt of carboxylic acid, $SO_3X$, or $PO_3X$, $R_{13}$ is a reactive group or a biomolecule, and $R_{14}$ is hydrogen or halogen.

In yet another preferred embodiment of the present invention the heterobifunctional dyes has the general formula:

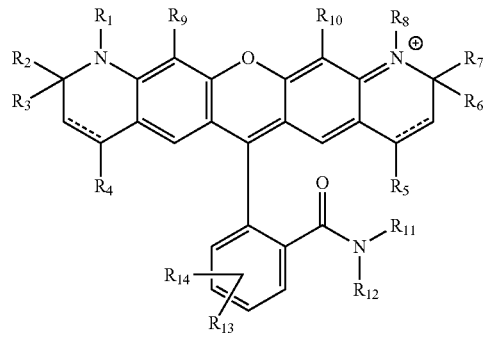

in which:

$R_1$, $R_2$, $R_3$, $R_6$, $R_7$ and $R_8$ are independently hydrogen, halogen, $SO_3X$, or $SO_2NH$—$(CH_2)_nSO_3X$, where n=2-5, and X is H or a counterion. Examples of suitable counterions include $K^+$, $Na^+$, $Cs^+$, $Li^+$, $Ca^{2+}$, $Mg^{2+}$, ammonium, alkylammonium, alkoxyammonium salts, or pyridinium salts.

$R_4$ and $R_5$ are independently hydrogen, $CH_3$, or $CH_2$—$SO_3X$, where X is H or counterion, $R_9$ and $R_{10}$ are independently hydrogen or $SO_3X$, where X is H or counterion, $R_{11}$ and $R_{12}$ are independently a reactive moiety partner of a pair of orthogonally reactive moieties that can react with each other in the presence or absence of a catalyst without activation and both reactive moieties are sufficiently stable under commonly applied biomolecule labeling conditions or $C_1$-$C_{18}$ alkyl further substituted with a carboxylic acid, a salt of carboxylic acid, $SO_3X$, or $PO_3X$, $R_{13}$ is a reactive group or a biomolecule, and $R_{14}$ is hydrogen or halogen.

Table 3 summarizes some of the preferred combinations of $R_{11}/R_{12}$ and $R_{13}$. These examples are not meant to be limiting but rather are representative of some more useful functionalities used in many biological applications.

TABLE 3

| $R_{11}/R_{12}$ | $R_{13}$ |
|---|---|
| NHS-ester | Trans-cyclooctene |
| NHS-ester | DBCO |

TABLE 3-continued

| $R_{11}/R_{12}$ | $R_{13}$ |
| --- | --- |
| NHS-ester | Azide |
| NHS-ester | Tetrazine |

To one skilled in the art, it will be apparent that there are multiple variations of reactive groups $R_{11}/R_{12}$ and $R_{13}$ useful for modifying a biomolecule with fluorescent dyes.

In still another aspect, the present invention relates to bio-orthogonal chemistry. The term bioorthogonal chemistry refers to any chemical reaction that can occur in the presence of rich functionalities of living systems/biological media without interfering with native biochemical processes. In this strategy, one component of the conjugate is modified with a bioorthogonal functional group, while in a separate reaction, the other component is activated with a complementary functional group of the bioorthogonal ligation pair. The two bioorthogonally-activated components are then mixed together and spontaneously react to form the specific conjugate. In certain embodiments, the bio-orthogonal reaction is a Cu-catalyzed version of Huisgen 1,3-dipolar cycloaddition between an azide and terminal alkyne. In other embodiments, the reaction is carried out in the absence of such a catalyst. Exemplary 1,3-dipole-functional compounds include, but are not limited to, azides, nitrile oxides, nitrones, and diazo compounds.

In another aspect, the present invention relates to trans-cyclooctenes and tetrazines. The inverse-electron demand Diels-Alder cycloaddition reaction of trans-cyclooctenes (TCO) with tetrazines is a bioorthogonal reaction that possesses exceptional kinetics (k>800 $M^{-1}$ $s^{-1}$) and selectivity. Such excellent reaction rate constants are unparalleled by any other bioorthogonal reaction pair described to date. Exemplary dienophile compounds include, but are not limited to, norbornene and trans-cyclooctenes.

By choosing appropriate click partners and fluorescent dyes, such compounds can be used for studying protein-protein interaction via FRET between dyes molecules.

In another embodiment of the present invention, a carboxamide-substituted dye has the following formula:

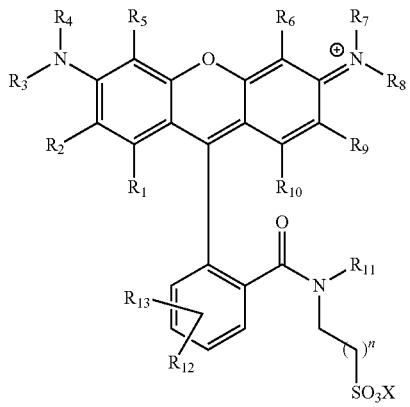

in which:
$R_1$, $R_2$, $R_9$ and $R_{10}$ are independently hydrogen or halogen,
$R_5$ and $R_6$ are independently hydrogen, $SO_3X$, or $SO_2NH$—$(CH_2)_n SO_3X$, where X is H or a counterion, and n=2-5,
$R_3$, $R_4$, $R_7$, and $R_8$ are independently H or $C_1$-$C_5$ alkyl, where each alkyl is optionally further substituted with halogen or $SO_3X$, where X is H or a counterion,
$R_{11}$ is $C_1$-$C_{18}$ alkyl, branched or cyclic saturated or unsaturated hydrocarbon group having up to 300 carbon atoms that is optionally interrupted by O or N atoms, optionally further substituted with F, Cl, Br, I, a carboxylic acid, a salt of carboxylic acid, or a carboxylic acid ester, $SO_3X$, or $PO_3X$, where X is H or a counterion,
$R_{12}$ is a reactive group, and
$R_{13}$ is hydrogen or halogen.

Preferably, $R_{11}$ may be discrete or non-discrete polyethylene glycol. Preferably, $R_{12}$ may be a biomolecule.

In yet another preferred embodiment, the present invention is directed to a carboxamide-substituted dye of the formula:

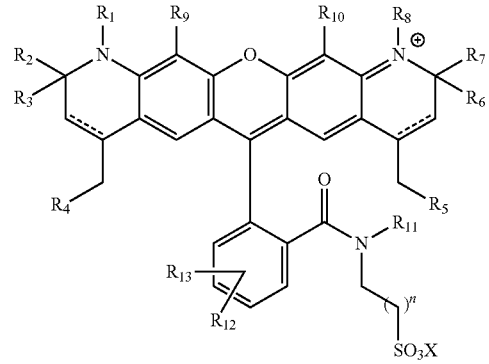

in which:
$R_1$, $R_2$, $R_3$, $R_6$, $R_7$, and $R_8$ are independently hydrogen, or $C_1$-$C_5$ alkyl, where each alkyl is optionally further substituted with halogen or $SO_3X$, where X is H or a counterion,
$R_9$ and $R_{10}$ are independently hydrogen, $SO_3X$, or $SO_2NH$—$(CH_2)_n SO_3X$, where X is H or a counterion, and n=2-5,
$R_4$ and $R_5$ are independently hydrogen, $CH_3$, or $SO_3X$, where X is H or counterion,
$R_{11}$ is $C_1$-$C_{18}$ alkyl, branched or cyclic saturated or unsaturated hydrocarbon group having up to 300 carbon atoms that is optionally interrupted by O or N atoms, optionally further substituted with F, Cl, Br, I, a carboxylic acid, a salt of carboxylic acid, or a carboxylic acid ester, $SO_3X$, or $PO_3X$, where X is H or a counterion,
$R_{12}$ is a reactive group, and
$R_{13}$ is hydrogen or halogen.

Preferably, $R_{11}$ may be discrete or non-discrete polyethylene glycol. Preferably, $R_{12}$ may be a biomolecule.

One embodiment of the invention is a method of synthesis of carboxamide dyes according to the general formula (I) or (II) comprising the following steps:

1. Condensation of the appropriate aminophenol with a methyl ester of trimellitic anhydride in the presence or absence of various acid catalysts or dehydrating agents. An aqueous workup, usually followed by column chromatography, yields a mixture of methyl esters of the desired dyes. The unsymmetrical xanthene dyes can also be constructed in a stepwise fashion wherein a selected aminophenol is condensed with a methyl ester of trimellitic anhydride in a 1:1 ratio to yield a benzophenone, which is optionally isolated, purified, and condensed with one equivalent of a different aminophenol, yielding the asymmetric dye.

2. Conversion of carboxylic acid at the 2' position of the "lower aromatic ring" into an activated ester with coupling reagents followed by a reaction with a secondary amine in the presence of non-nucleophilic bases, preferably at ambient temperature. The preferred activating agent is HATU, and the preferred non-nucleophilic base is triethylamine. Optionally, the activated ester can be isolated.

3. Conversion of the methyl ester group of the carboxamide dyes obtained in step 2 into a carboxylic acid. At this step, the reaction should be very carefully controlled since a prolonged reaction time will result in partial to full cleavage of the secondary amide group.

Optionally, the carboxylic acid obtained in step 2 can be converted into an activated ester or coupled to primary amines in the presence of activating agents well known in the art.

Yet another embodiment of the invention relates to the use of inventive carboxamide dyes according to the general formula (I). The preparation of a dye conjugated using reactive dyes is well documented. See, for examples of such methods: Hermanson, G. T., Bioconjugate Techniques, Elsevier Science, London, 2008. Conjugates typically result from mixing appropriate reactive dyes and the substance to be conjugated in a suitable solvent in which both are soluble.

For biological applications, the carboxamide dye of the invention is typically used in mostly aqueous media or aqueous-miscible solutions prepared according to methods generally known in the art. The exact concentration of the dye component depends on the experimental conditions and the desired result, but typically ranges from about one nanomolar to one millimolar or more. The optimal concentration is determined experimentally. It is also preferred that the labeled antibody be purified by dialysis or by gel permeation chromatography to remove any unconjugated compounds. One of ordinary skill in the art would know ways and means of purification.

In one aspect, biomolecules can be labeled according to the present invention by means of a kit. In certain instances, the kit comprises a buffer, a compound as disclosed in the instant application, purification media, and the manual. Preferably, the kit contains a coupling buffer such as 1 M $KH_2PO_4$ (pH 5), optionally with added acid or base to modify the pH (e.g., pH 7.5 is preferred for reactions with succinimide esters and pH 6.5 is preferred for reactions with maleimides).

Conjugates having an ion-complexing moiety might be used as indicators for calcium, sodium, zinc or other biologically important metal ions. Exemplary ion-complexing moieties are crown ethers, including diaryldiaza crown ethers (U.S. Pat. No. 5,405,975), and BAPTA chelators (U.S. Pat. No. 5,453,517).

While the invention has been described with references to a preferred embodiments, those skilled in the art will understand various changes may be made and equivalents may be substituted for elements thereof without departing from the scope of the invention. In addition, many modifications may be made to adapt a particular situation or materials to the teaching of the invention without departing from the essential scope thereof. Therefore, it is intended that the invention not to be limited to the particular embodiments disclosed but that the invention will include all embodiments falling within the scope of the appended claims. In this application, all units are in the metric system, and all amounts and percentages are by weight, unless otherwise expressly indicated. Also, all citations referred to herein are expressly incorporated herein by reference.

The following examples are offered to illustrate various embodiments of the invention but should not be viewed as limiting the scope of the invention.

EXAMPLES

Example 1

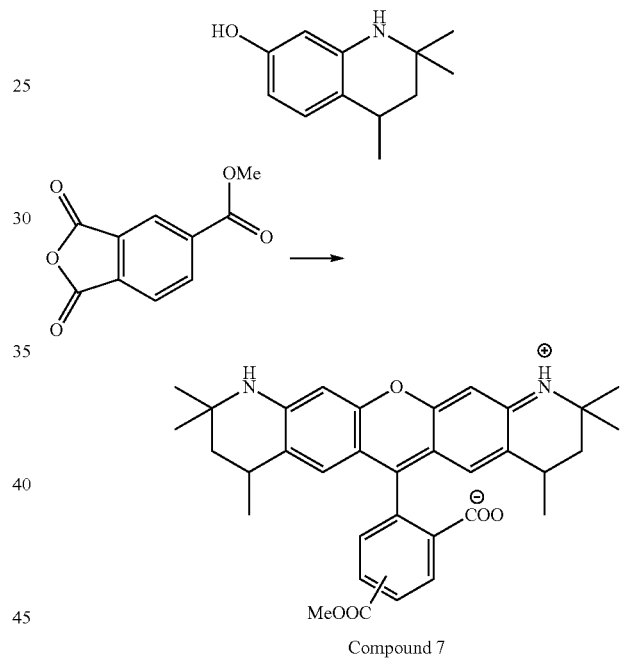

Compound 7

A solution of 2,2,4-trimethyl-1,2,3,4-tetrahydroquinolin-7-ol (2 g, 10.46 mmol) was heated to ca. 70° C. and cooled to room temperature. Methyl 1,3-dioxo-1,3-dihydroisobenzofuran-5-carboxylate (2.156 g, 10.46 mmol) was added, and the reaction mixture was brought to reflux. The reaction mixture was refluxed overnight. According to TLC analysis, one major, non-fluorescent product was formed, and a small amount of highly fluorescent compound was also detected by TLC. The reaction mixture was concentrated under reduced pressure, DMF (25 mL) was added, 2,2,4-trimethyl-1,2,3,4-tetrahydroquinolin-7-ol (2 g, 10.46 mmol) and triethylsilylpolyphosphate (dehydrating agent, 12 mL) were added, and the reaction mixture was refluxed for ca. 60 min. Upon completion, the reaction mixture was cooled to room temperature and concentrated under reduced pressure to provide an oily compound that became semi-solid upon standing at room temperature. The crude product (ca. 3 g) was purified on silica gel (DCM:MeOH 10:1) to provide 1.35 g of Compound 7 as a red solid.

Example 2

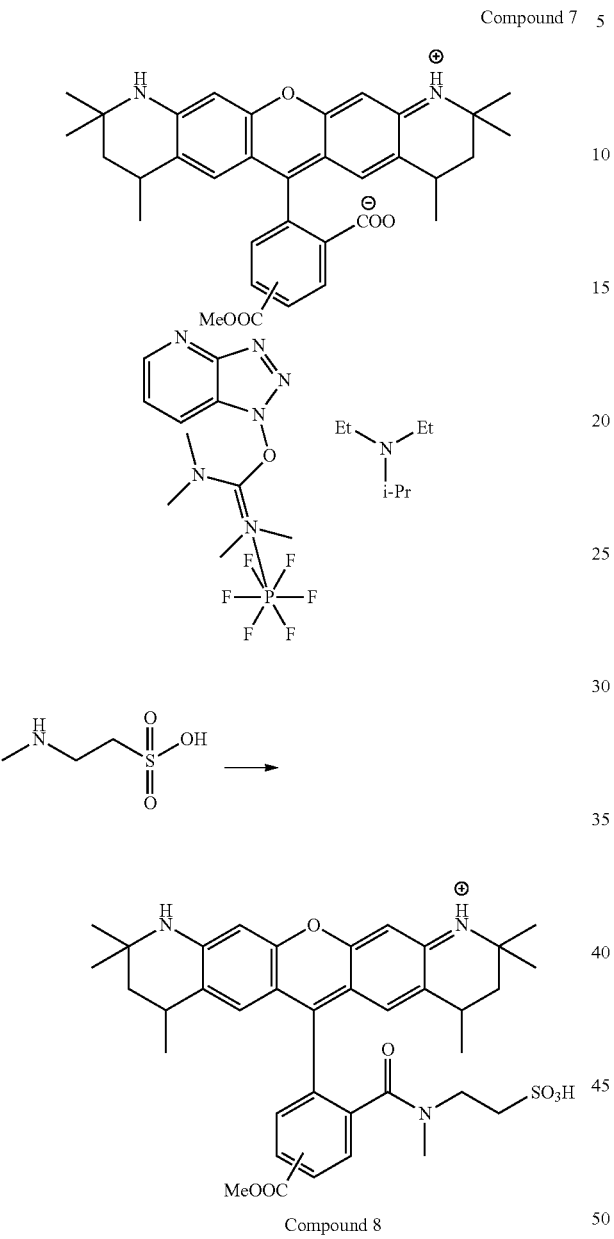

Compound 7
Compound 8

HATU (2.91 g, 7.64 mmol) was added to a solution of Compound 7 (3.25 g, 5.88 mmol) and N,N-diethylpropan-2-amine (2.033 g, 17.64 mmol) in DMF (50 ml) at room temperature, and the reaction mixture was stirred for ca. 30 min at room temperature. A suspension of 2-(methylamino) ethanesulfonic acid (0.982 g, 7.06 mmol) and DIEA (ca. 2 mL) was added to the reaction mixture, and the reaction mixture was stirred overnight at room temperature. According to TLC analysis, all of the substrate was consumed, and one product was detected by TLC. The reaction mixture was concentrated under reduced pressure to provide an oily compound. The crude product was purified on silica gel (DCM:MeOH 10:1 to 3:1) to provide 3.7 g of Compound 8 as a red solid.

Example 3

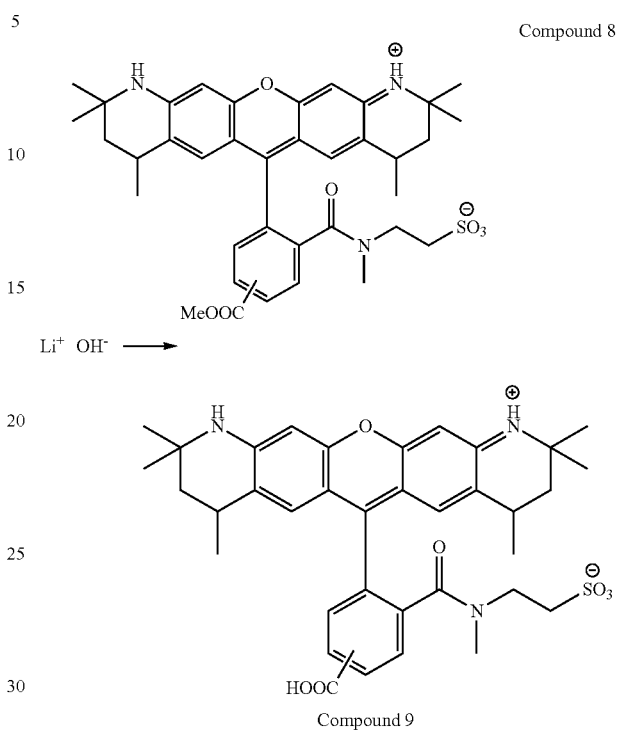

Compound 8
Compound 9

A solution of lithium hydroxide (0.960 g, 27.4 mmol) in water (7.50 ml) was added to a solution of Compound 8 (3.7 g, 5.48 mmol) in MeOH (15 ml), and the reaction mixture was stirred for ca. 60 min. According to TLC analysis, all of the substrate was consumed, and a small amount of diacid was formed by hydrolysis of the amide group. Prolonged reaction time usually results in substantial formation of the diacid. The reaction mixture was concentrated under reduced pressure to provide crude 9 as a red solid. The crude product was purified on silica gel (DCM:MeOH 10:1 to 3:1+0.5% AcOH) to provide 1.4 g of Compound 9 as a red solid.

Example 4

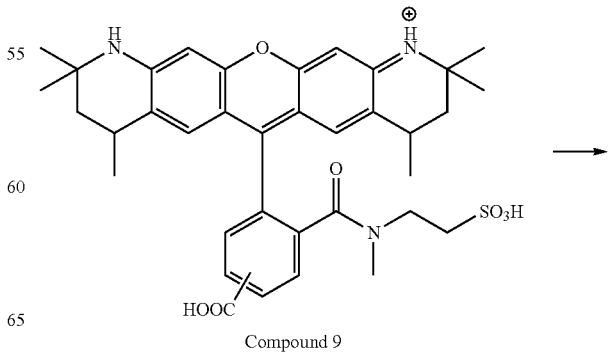

Compound 9

21

-continued

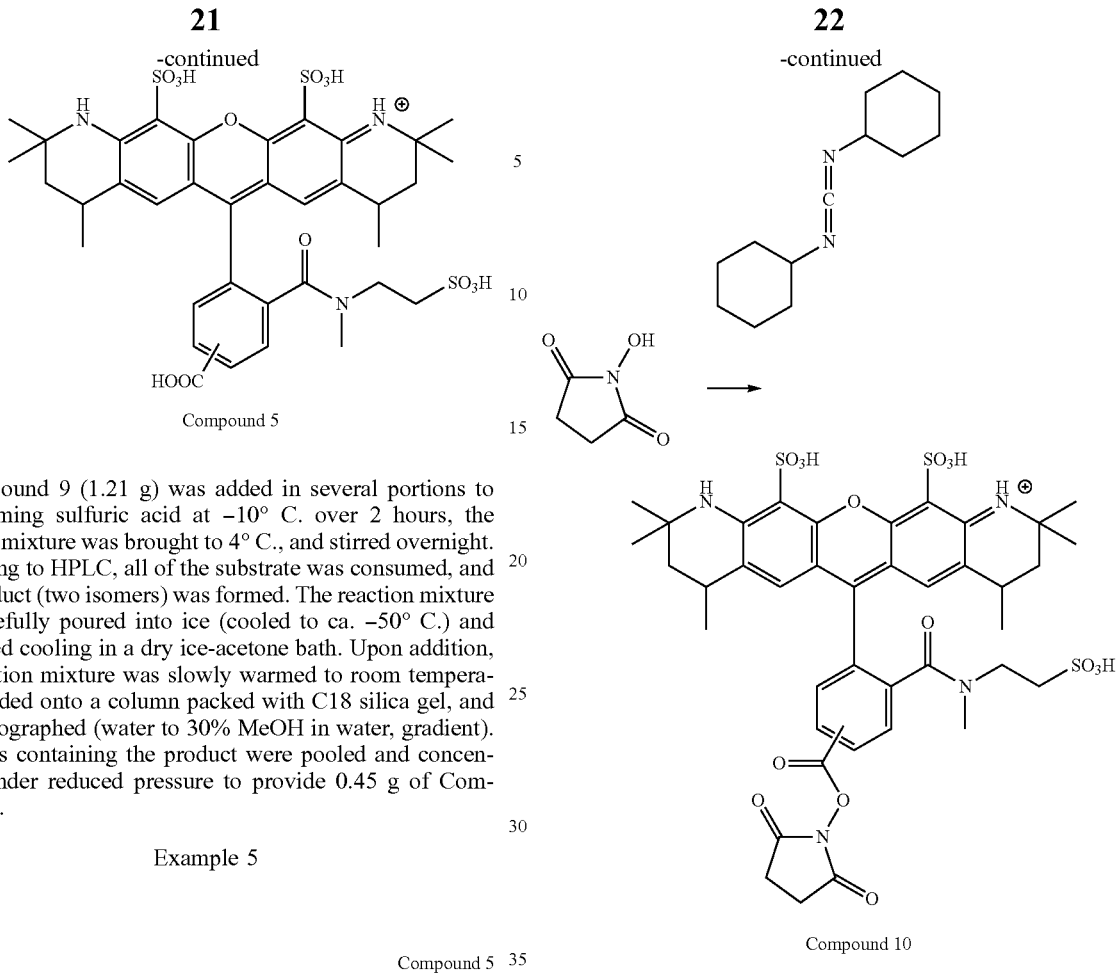

Compound 5

Compound 9 (1.21 g) was added in several portions to 30% fuming sulfuric acid at −10° C. over 2 hours, the reaction mixture was brought to 4° C., and stirred overnight. According to HPLC, all of the substrate was consumed, and one product (two isomers) was formed. The reaction mixture was carefully poured into ice (cooled to ca. −50° C.) and continued cooling in a dry ice-acetone bath. Upon addition, the reaction mixture was slowly warmed to room temperature, loaded onto a column packed with C18 silica gel, and chromatographed (water to 30% MeOH in water, gradient). Fractions containing the product were pooled and concentrated under reduced pressure to provide 0.45 g of Compound 5.

Example 5

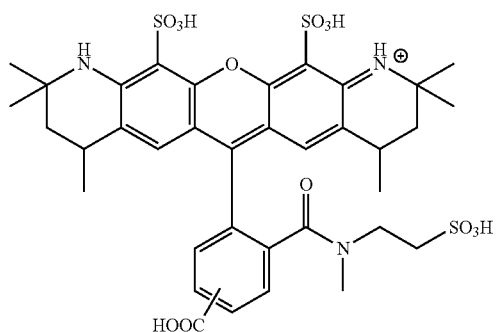

Compound 5

22

-continued

DCC (0.102 g, 0.493 mmol) was added to a solution of Compound 5 (0.3 g) and NHS (0.048 g, 0.42 mmol) in DMF (20 mL) at room temperature, and the reaction mixture was stirred overnight. According to HPLC, all of the acid was converted into NHS ester. The reaction mixture was placed into a refrigerator for 24 hours, and the precipitate was filtered. The reaction mixture was poured into EtOAc (150 mL) and stirred for ca. an hour. The precipitate was filtered, washed with EtOAc, and dried on an oil pump to provide 320 mg of Compound 10.

Example 6

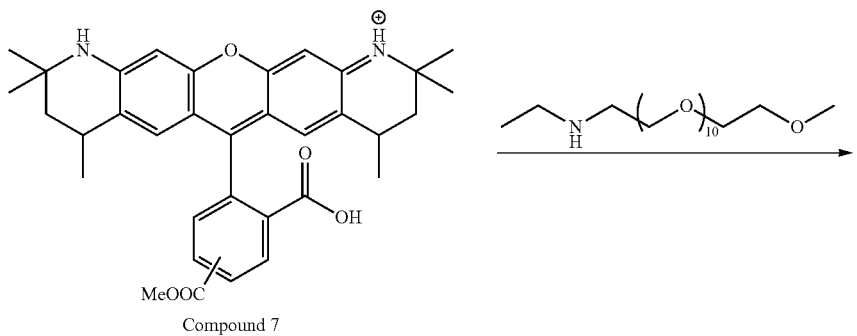

Compound 7

-continued

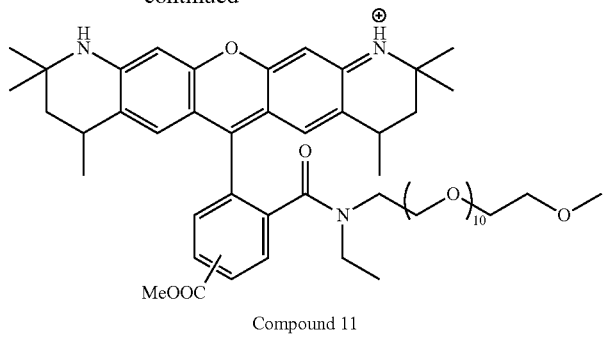

Compound 11

HATU (2.16 g, 5.66 mmol) was added to a solution of Compound 7 (2.41 g, 4.36 mmol) and N,N-diethylpropan-2-amine (1.5 mL) in DMF (30 ml) at room temperature, and the reaction mixture was stirred for ca. 30 min at room temperature. A solution of ethyl-mPEG11 amine (3.9 g) was added to the reaction mixture, and the reaction mixture was stirred overnight at room temperature. According to TLC analysis, all of the substrate was consumed, and one product was detected by TLC. The reaction mixture was concentrated under reduced pressure to provide an oily compound. The crude product was purified on silica gel (DCM:MeOH 15:1 to 10:1) to provide 2.1 g of Compound 11 as a red solid.

Example 7

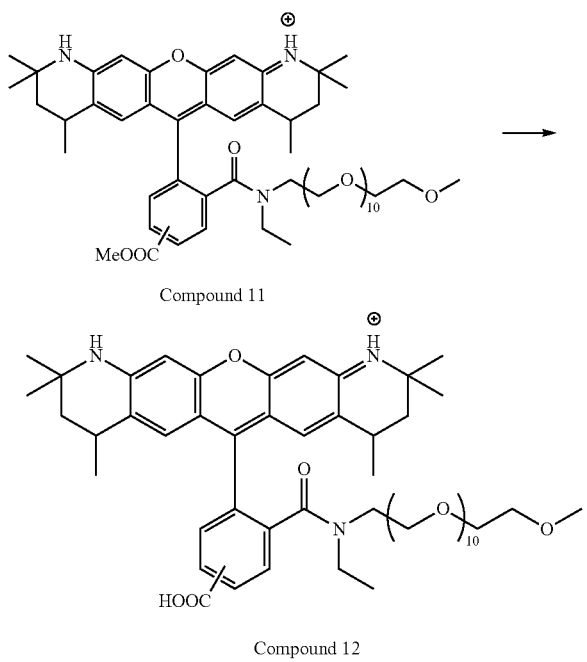

A solution of lithium hydroxide (0.686 g, 19.6 mmol) in water (5 ml) was added to a solution of Compound 11 (2.0 g) in MeOH (10 ml), and the reaction mixture was stirred for ca. 60 min. According to TLC analysis, all of the substrate was consumed, and some amount of diacid was formed. Prolonged reaction time usually results in substantial formation of the diacid. The reaction mixture was concentrated under reduced pressure to provide crude 12 as a red solid. The crude product was purified on silica gel (DCM:MeOH 15:1 to 5:1+0.5% AcOH) to provide 0.78 g of Compound 12 as a red solid.

Example 8

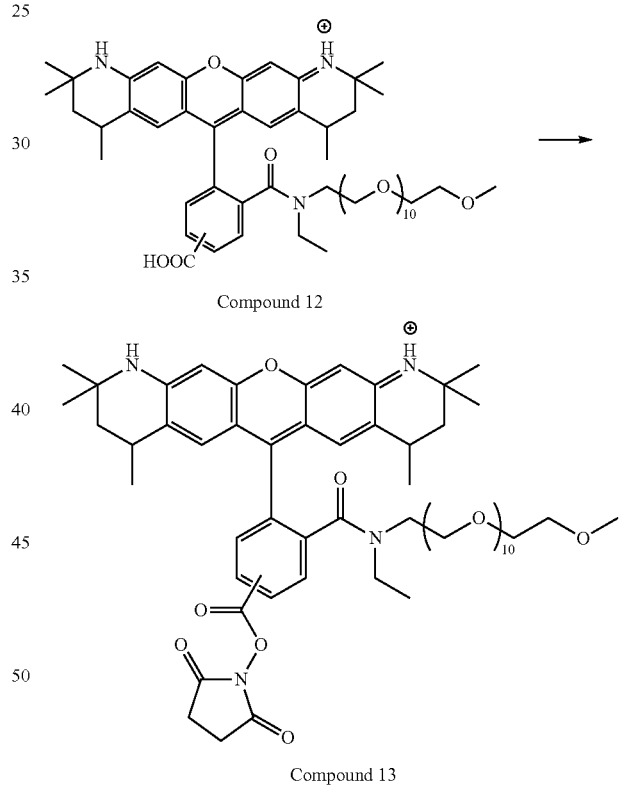

DCC (0.5 g, 2.49 mmol) was added to a solution of Compound 12 (0.78 g) and NHS (0.2 g, 2.10 mmol) in DMF (10 mL) at room temperature, and the reaction mixture was stirred overnight. According to HPLC, all of the acid was converted into NHS ester. The reaction mixture was placed into a refrigerator for 24 hours, and the precipitate was filtered. The reaction mixture was concentrated under reduced pressure and chromatographed on silica gel (DCM:MeOH 10:1 to 5:1+0.5% AcOH) to provide 436 mg of Compound 13.

Example 9

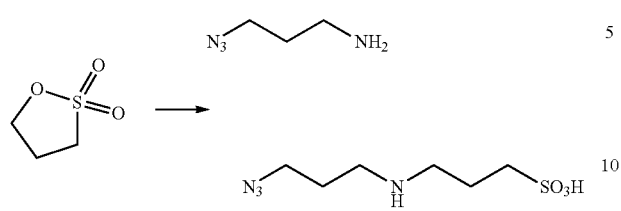

A solution of 3-azidopropan-1-amine (2 g, 19.98 mmol) and 1,2-oxathiolane 2,2-dioxide (2.440 g, 19.98 mmol) in DCM (10 mL) was stirred overnight at room temperature. A white precipitate was filtered and washed with a small amount of THF-Et$_2$O and dried on an oil pump to provide 2.35 g of 3-((3-azidopropyl)amino)propane-1-sulfonic acid.

Example 10

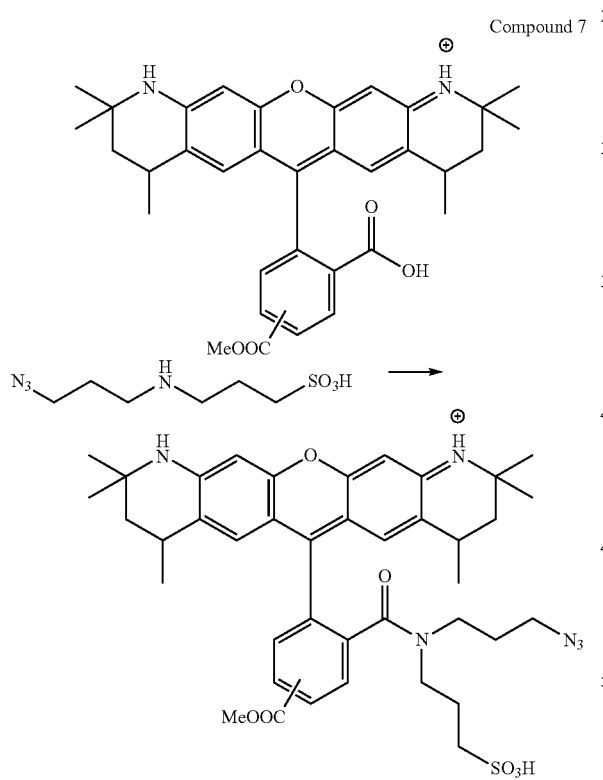

Compound 14

HATU (0.894 g, 2.352 mmol) was added to a solution of Compound 7 (1 g, 1.809 mmol) and N,N-diethylpropan-2-amine (0.625 g, 5.43 mmol) in DMF (15 ml) at room temperature, and the reaction mixture was stirred for ca. 30 min. A suspension of 3-((3-azidopropyl)amino)propane-1-sulfonic acid (0.422 g, 1.900 mmol) and DIEA (ca. 0.5 mL) was added, and the reaction mixture was stirred overnight at room temperature. According to TLC analysis, all of the substrate was converted into product. The reaction mixture was concentrated under reduced pressure and chromatographed on silica gel (DCM:MeOH 20:1 to 10:1 to 5:1) to provide 0.61 g of Compound 14.

Example 11

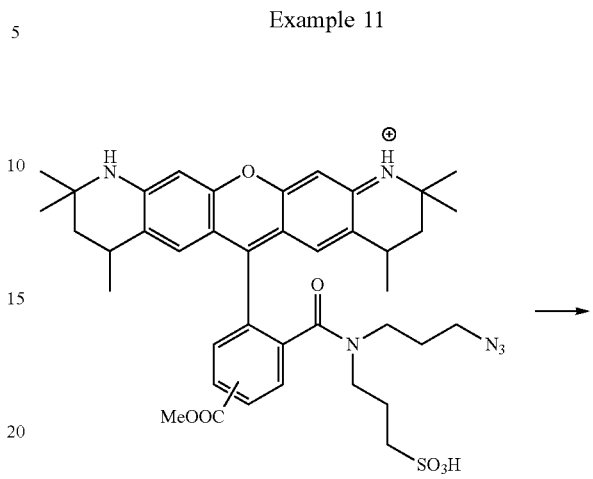

Compound 14

Compound 15

Compound 14 was converted into Compound 15 in the same way that Compound 11 was converted into Compound 13.

Example 12

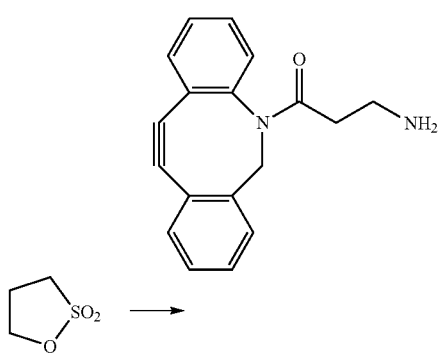

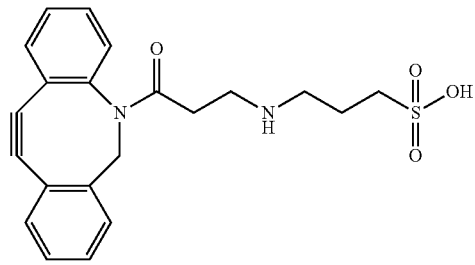

Compound 16

A solution of DBCO-Amine (4 g, 14.48 mmol) (Click Chemistry Tools, Scottsdale, Ariz.) and 1,2-oxathiolane 2,2-dioxide (1.591 g, 13.03 mmol) in DCM (20 mL) was stirred overnight at room temperature. A white precipitate was filtered, washed with a small amount of THF-Et$_2$O, and dried on an oil pump to provide 3.53 g (8.86 mmol, 61%) of Compound 16.

Example 13

HATU (0.395 g, 1.039 mmol) was added to a solution of Compound 7 (0.5 g, 0.903 mmol) and N,N-diethylpropan-2-amine (0.312 g, 2.71 mmol) in DMF (10 ml) at room temperature, and the reaction mixture was stirred for ca. 30 min. A suspension of Compound 16 (0.360 g, 0.903 mmol) and DIEA (ca. 0.3 mL) was added, and the reaction mixture was stirred overnight at room temperature. According to TLC analysis, all of the substrate was converted into product. The reaction mixture was concentrated under reduced pressure and chromatographed on silica gel (DCM:MeOH 20:1 to 10:1 to 5:1) to provide 0.60 g (0.624 mmol, 71%) of Compound 17.

Example 14

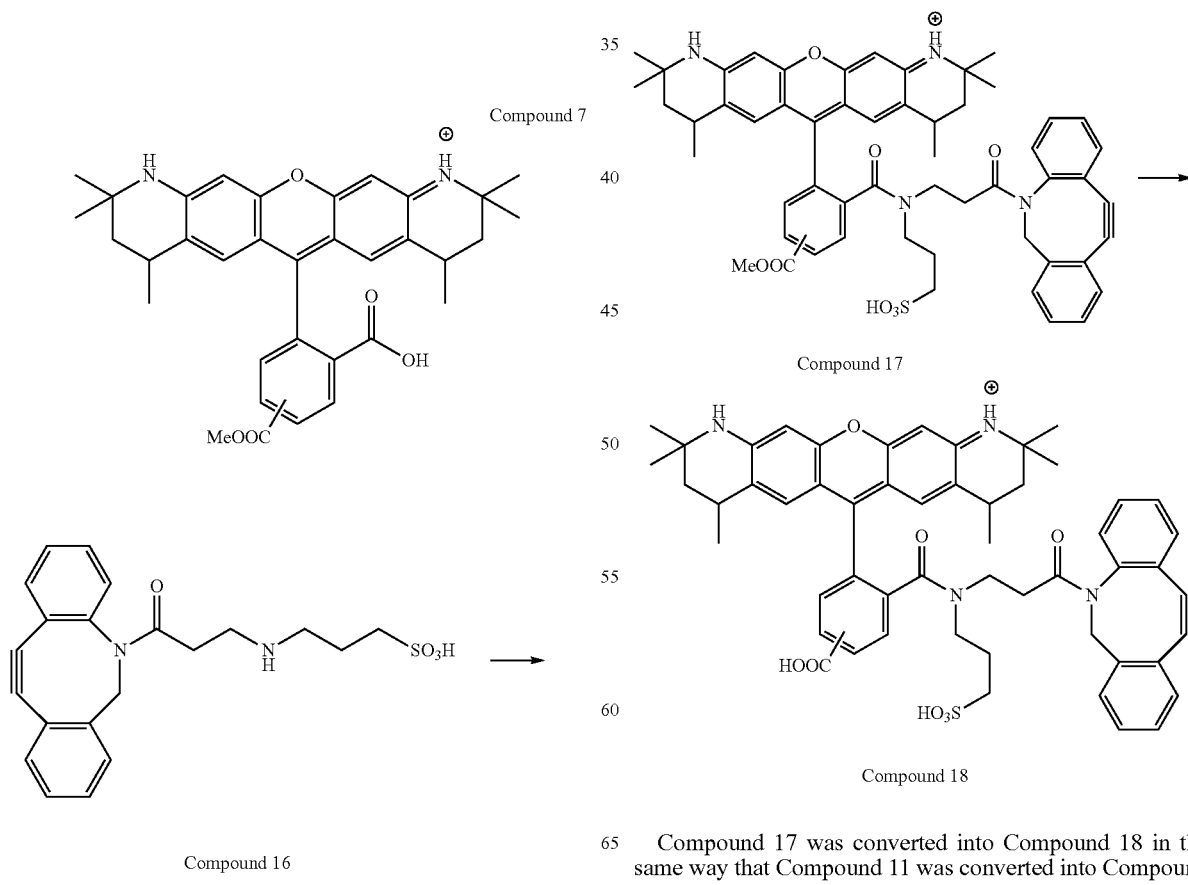

Compound 17 was converted into Compound 18 in the same way that Compound 11 was converted into Compound 13.

Compound 19

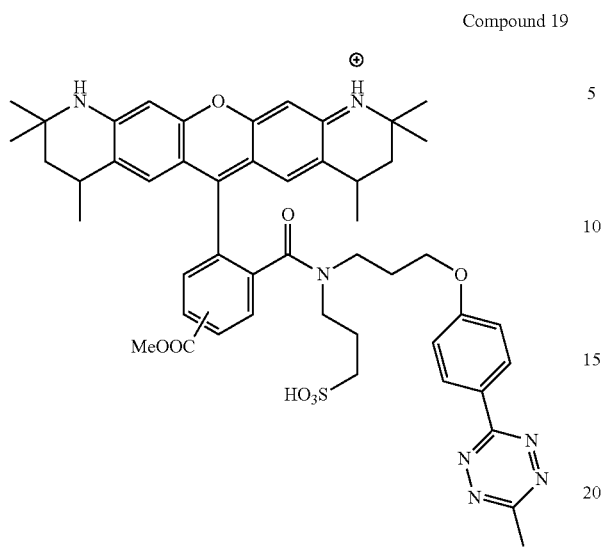

Compound 20

Compounds 19 and 20 were prepared from commercially available TCO-Amine and tetrazine-amine using the procedure described in Examples 12, 13, and 14.

Compound 1, 2, and 6 were prepared in the same way as dyes 3, 4, or 5 using corresponding aminophenols. The corresponding aminophenols were prepared according to syntheses known from the literature or processes known to the skilled person.

Example 15

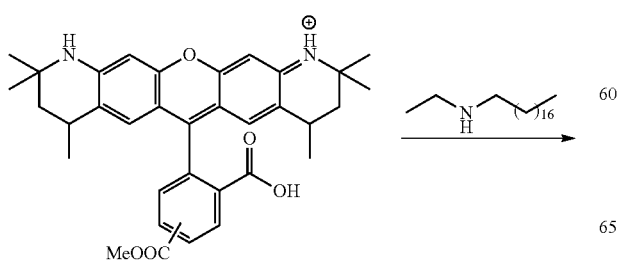

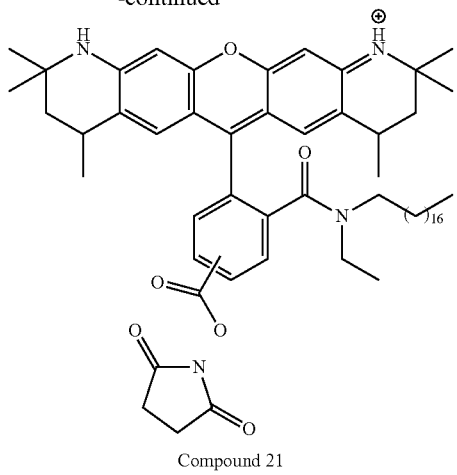

Compound 21

Compound 21 was prepared according to Examples 6, 7, and 8.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

The invention claimed is:

1. A carboxamide-substituted dye of the formula (I)

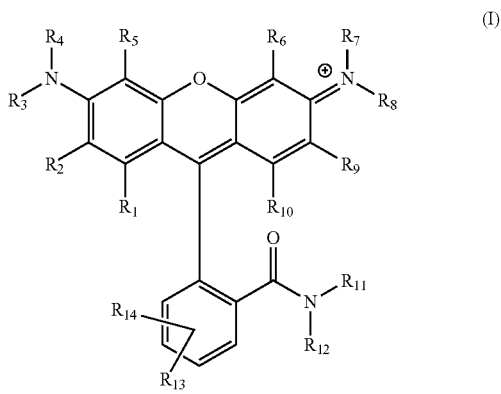

in which:
- $R_1$ and $R_{10}$ are hydrogen,
- $R_2$ and $R_9$ are independently hydrogen or halogen,
- $R_5$ and $R_6$ are independently hydrogen, $SO_3X$, or $SO_2NH-(CH_2)_n-SO_3X$, and n=2-5,
- $R_3$, $R_4$, $R_7$, and $R_8$ are independently H or $C_1$-$C_5$ alkyl, where each alkyl is optionally further substituted with halogen or $SO_3X$, or
- $R_3$ in combination with $R_2$ form a 5- or 6-membered saturated or unsaturated ring that is optionally substituted with a $C_1$-$C_5$ alkyl, where each alkyl is optionally further substituted with $SO_3X$, or
- $R_8$ in combination with $R_9$ form a 5- or 6-membered saturated ring that is optionally substituted with a $C_1$-$C_5$ alkyl, where each alkyl is optionally further substituted with $SO_3X$,
- X is H or a counterion,
- $R_{11}$ and $R_{12}$ are polyethylene glycol, R_13 is N-hydroxysuccinimidyl, p-nitrophenyl, pentafluorophenyl, N-hydroxybenzotriazolyl ester, maleimido, alpha-haloacetamido, pyridyldisulfides, carbodiimide, carbonyl, diazirine, hydrazide, hydroxymethyl phosphine, imidoester, NHS-ester, PFP-ester, psoralen, pyridyl disulfide, vinyl sulfone, terminal alkyne, azide, trans-cyclooctene, or a biomolecule selected from the group consisting of a nucleic acid, a nucleotide, a protein, an amino acid, a carbohydrate monomer, or a polysaccharide, and $R_{14}$ is hydrogen.

2. The compound according to claim 1, wherein $R_{13}$ is a biomolecule selected from the group consisting of a protein and a nucleotide.

3. A carboxamide-substituted dye of the formula:

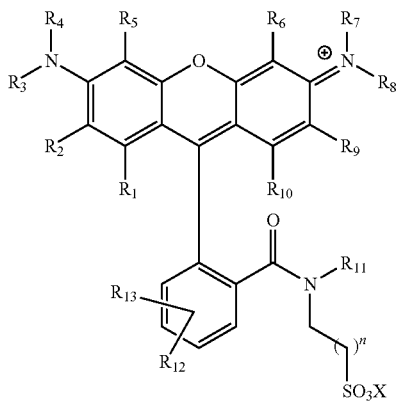

in which:
- $R_1$, $R_2$, $R_9$ and $R_{10}$ are independently hydrogen or halogen,
- $R_5$ and $R_6$ are independently hydrogen, $SO_3X$, or $SO_2NH$—$(CH_2)_n$—$SO_3X$, where X is H or a counterion, and n=2-5,
- $R_3$, $R_4$, $R_7$, and $R_8$ are independently H or $C_1$-$C_5$ alkyl, where each alkyl is optionally further substituted with halogen or $SO_3X$, where X is H or a counterion,
- $R_{11}$ is $C_1$-$C_{18}$ alkyl or a branched or cyclic saturated or unsaturated hydrocarbon group having up to 300 carbon atoms, any one of which is optionally interrupted by O or N atoms, optionally further substituted with F, Cl, Br, I, a carboxylic acid, a salt of carboxylic acid, or a carboxylic acid ester, $SO_3X$, or $PO_3X$, where X is H or a counterion,
- $R_{12}$ is a N-hydroxysuccinimidyl, p-nitrophenyl, pentafluorophenyl, N-hydroxybenzotriazolyl ester, maleimido, alpha-haloacetamido, pyridyldisulfides, carbodiimide, carbonyl, diazirine, hydrazide, hydroxymethyl phosphine, imidoester, NHS-ester, PFP-ester, psoralen, pyridyl disulfide, vinyl sulfone, terminal alkyne, azide, trans-cyclooctene, or a biomolecule selected from the group consisting of a nucleic acid, a nucleotide, a protein, an amino acid, a carbohydrate monomer, or a polysaccharide, and
- $R_{13}$ is hydrogen or halogen.

4. The compound according to claim 3, wherein $R_{11}$ is polyethylene glycol.

5. A carboxamide-substituted dye of the formula:

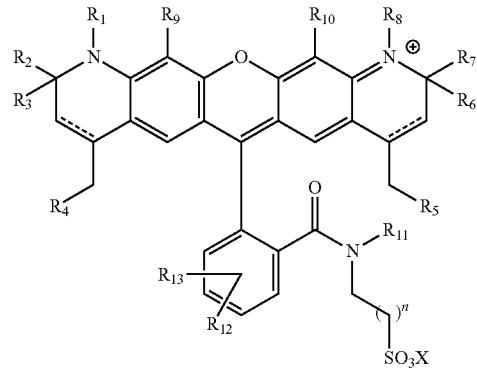

in which:
- $R_1$, $R_2$, $R_3$, $R_6$, $R_7$, and $R_8$ are independently hydrogen, or $C_1$-$C_5$ alkyl, where each alkyl is optionally further substituted with halogen or $SO_3X$, where X is H or a counterion,
- $R_9$ and $R_{10}$ are independently hydrogen, $SO_3X$, or $SO_2NH$—$(CH_2)_n$—$SO_3X$, where X is H or a counterion, and n=2-5,
- $R_4$ and $R_5$ are independently hydrogen, $CH_3$, or $SO_3X$, where X is H or counterion,
- $R_{11}$ is $C_1$-$C_{18}$ alkyl or a branched or cyclic saturated or unsaturated hydrocarbon group having up to 300 carbon atoms, any one of which is optionally interrupted by 0 or N atoms, optionally further substituted with F, Cl, Br, I, a carboxylic acid, a salt of carboxylic acid, or a carboxylic acid ester, $SO_3X$, or $PO_3X$, where X is H or a counterion,
- $R_{12}$ is a N-hydroxysuccinimidyl, p-nitrophenyl, pentafluorophenyl, N-hydroxybenzotriazolyl ester, maleimido, alpha-haloacetamido, pyridyldisulfides, carbodiimide, carbonyl, diazirine, hydrazide, hydroxymethyl phosphine, imidoester, NHS-ester, PFP-ester, psoralen, pyridyl disulfide, vinyl sulfone, terminal alkyne, azide, trans-cyclooctene, or a biomolecule selected from the group consisting of a nucleic acid, a nucleotide, a protein, an amino acid, a carbohydrate monomer, or a polysaccharide, and
- $R_{13}$ is hydrogen or halogen.

6. The compound according to claim 5, wherein $R_{11}$ is polyethylene glycol.

* * * * *